(12) United States Patent
Itsuji

(10) Patent No.: US 7,919,752 B2
(45) Date of Patent: Apr. 5, 2011

(54) INSPECTION APPARATUS AND INSPECTION METHOD BY USING TERAHERTZ WAVE

(75) Inventor: Takeaki Itsuji, Hiratsuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 281 days.

(21) Appl. No.: 12/359,225

(22) Filed: Jan. 23, 2009

(65) Prior Publication Data
US 2009/0189078 A1 Jul. 30, 2009

(30) Foreign Application Priority Data
Jan. 29, 2008 (JP) ................................. 2008-017844

(51) Int. Cl.
G01N 21/35 (2006.01)
G01N 21/31 (2006.01)
(52) U.S. Cl. ............. 250/339.06; 250/341.1; 250/341.8
(58) Field of Classification Search ............. 250/339.06, 250/341.1, 341.8
See application file for complete search history.

(56) References Cited

U.S. PATENT DOCUMENTS

| | | | |
|---|---|---|---|
| 6,078,047 A | 6/2000 | Mittleman et al. | 250/338.1 |
| 6,448,553 B1 | 9/2002 | Itsuji et al. | 250/306 |
| 6,835,925 B2 | 12/2004 | Itsuji et al. | 250/234 |
| 7,248,995 B2 | 7/2007 | Itsuji et al. | 702/159 |
| 7,358,918 B2 | 4/2008 | Itsuji | 343/772 |
| 2005/0082479 A1 | 4/2005 | Wallace et al. | 250/330 |
| 2005/0156120 A1* | 7/2005 | Arnone et al. | 250/492.2 |
| 2005/0231416 A1* | 10/2005 | Rowe et al. | 342/22 |
| 2006/0140637 A1* | 6/2006 | Sakata et al. | 398/147 |
| 2007/0030115 A1 | 2/2007 | Itsuji et al. | 340/5.8 |
| 2007/0235718 A1 | 10/2007 | Kasai et al. | 257/21 |
| 2008/0161674 A1* | 7/2008 | Monro | 600/410 |
| 2008/0165062 A1 | 7/2008 | Itsuji | 343/700 |
| 2008/0186239 A1 | 8/2008 | Itsuji | 343/700 |
| 2008/0315098 A1 | 12/2008 | Itsuji | 250/330 |
| 2009/0009190 A1 | 1/2009 | Itsuji | 324/639 |

FOREIGN PATENT DOCUMENTS

| | | |
|---|---|---|
| DE | 10 2005 023160 | 11/2006 |
| GB | 2410081 | 7/2005 |
| GB | 2438215 | 11/2007 |
| JP | 11-108845 | 4/1999 |

OTHER PUBLICATIONS

Extended European Search Report dated May 11, 2009, from corresponding European Application No. 09150532.1.
Ferguson B. et al., "De-Noising Techniques for Terahertz Responses of Biological Samples" Microelectronics Journal, vol. 32, 2001, pp. 943-953.
U.S. Appl. No. 12/326,037, filed Dec. 1, 2008, Inventor: Takeaki Itsuji.

* cited by examiner

*Primary Examiner* — David P Porta
*Assistant Examiner* — Jessica L Eley
(74) *Attorney, Agent, or Firm* — Fitzpatrick, Cella, Harper & Scinto

(57) ABSTRACT

An inspection apparatus includes a terahertz wave detection portion, a waveform shaping portion configured to shape a first answer signal with respect to a terahertz wave by using a signal acquired in the above-described terahertz wave detection portion, a measurement condition acquisition portion configured to acquire a first measurement condition, an answer signal storage portion configured to store second answer signals corresponding to measurement conditions, a selection portion configured to select the above-described second answer signal from the above-described answer signal storage portion, and a signal processing portion configured to conduct deconvolution with respect to the above-described first answer signal on the basis of the above-described second answer signal.

7 Claims, 15 Drawing Sheets

INSPECTION APPARATUS AND INSPECTION METHOD BY USING TERAHERTZ WAVE

BACKGROUND OF THE INVENTION

1. Field of the Invention

The present invention relates to an inspection apparatus and an inspection method, and more particularly to conducting an inspection of an object to be measured by using a terahertz wave.

2. Description of the Related Art

The terahertz wave refers to an electromagnetic wave having any frequency band within the range of 0.03 THz to 30 THz. In the terahertz wave band, there are characteristic absorptions derived from structures and states of living body molecules and other various substances. Inspection technologies for conducting nondestructive analysis and identification of substances taking advantage of such characteristics have been developed. Furthermore, application to a safe imaging technology in place of X-rays and a high-speed communication technology may be expected.

Regarding such imaging technology, an apparatus which acquires information of an object to be measured in a depth direction has been developed. This apparatus derives a spike-shaped time waveform by conducting deconvolution based on a perfect reflection waveform of a terahertz wave with respect to a terahertz reflection waveform from the object to be measured. Here, an example of imaging in the inside of FLOPPY (registered trade mark) is demonstrated, wherein an improvement in resolution is intended by determining a refractive index interface through the use of the spike-shaped time waveform. A form in which a terahertz wave measured through replacement with a mirror or other substances that conduct reflection while a loss is substantially zero is used as a perfect reflection waveform of terahertz wave is disclosed in FIG. 2 of Japanese Patent Laid-Open No. 11-108845 (Corresponding to U.S. Pat. No. 6,078,047, hereinafter Patent Document 1).

SUMMARY OF THE INVENTION

If the apparatus disclosed in Patent Document 1 is applied to an inspection apparatus which inspects an object to be measured for a long time, the following problems are typically expected. That is, since it is not taken into consideration that the perfect reflection waveform of a terahertz wave is changed because of fluctuation in a terahertz wave light source and secular changes in inspection environments, e.g., temperature and humidity, the measurement accuracy may become poor because of the fluctuation and the like.

Specifically, regarding the above-described apparatus, if the perfect reflection waveform of a terahertz wave is not properly selected, the spike-shaped time waveform may not properly reflect the state of the object to be measured. As a result, deterioration in reliability of the inspection itself may occur.

Consequently, in order to suppress such secular changes in the inspection environment, it is conceived that units (for example, a unit configured to evacuate the inspection environment and a unit configured to substitute the inspection environment with a predetermined gas) configured to make the inspection environment constant can be applied.

Regarding this form, however, it is necessary to separate the inspection environment from the outside environment. Therefore, it can be expected that the shape of the object to be measured and the inspection environment are limited and, thereby, the versatility of the apparatus is impaired.

In the assumption disclosed in Patent Document 1, as for a perfect reflection waveform of a terahertz wave, a measurement is conducted through replacement with a mirror or other substances that conduct reflection while a loss is substantially zero. In order to avoid application of the above-described unit configured to make the inspection environment constant, a form is conceived in which this mirror and the object to be measured is switched sequentially so as to renew the perfect reflection waveform of the terahertz wave. However, an additional inspection time for this series of operations is required. Consequently, it is expected that places for application of the inspection apparatus are limited and the versatility of the apparatus is impaired.

As described above, regarding the inspection apparatus of terahertz wave, a new inspection apparatus which can respond to changes in an inspection environment and the like and which is highly versatile is provided.

An inspection apparatus for conducting inspection of an object to be measured by using a terahertz wave, according to a first aspect of the present invention, includes a terahertz wave generation portion, a terahertz wave detection portion configured to detect a terahertz wave applied from the terahertz wave generation portion to the object to be measured, the terahertz wave being detected through the object to be measured, a waveform shaping portion configured to shape a first answer signal with respect to the terahertz wave by using a signal acquired in the above-described terahertz wave detection portion, a measurement condition acquisition portion configured to acquire a first measurement condition, an answer signal storage portion configured to store second answer signals associated with the measurement conditions, a selection portion configured to select the above-described second answer signal from the above-described answer signal storage portion by using the above-described first measurement condition, and a signal processing portion configured to conduct deconvolution with respect to the above-described first answer signal on the basis of the above-described second answer signal.

An inspection method by using a terahertz wave, according to a second aspect of the present invention, includes the steps of shaping a waveform serving as a first answer signal by detecting the terahertz wave applied to an object to be measured, the terahertz wave being detected through the object to be measured, and acquiring a measurement condition, wherein deconvolution with respect to the above-described first answer signal is conducted by using a second answer signal corresponding to the above-described acquired measurement condition.

A new inspection apparatus which can respond changes in the inspection environment and the like and which is highly versatile can be provided on the basis of the inspection apparatus according to the first aspect of the present invention.

Further features of the present invention will become apparent from the following description of exemplary embodiments with reference to the attached drawings.

DESCRIPTION OF THE EMBODIMENTS

The embodiments for executing the present invention will be described below with reference to the drawings.

First Embodiment: Inspection Apparatus

The present embodiment shows one form of an inspection apparatus by using a terahertz wave according to a first aspect of the present invention.

The inspection apparatus is configured to include a terahertz wave generation portion and a terahertz wave detection portion configured to detect a terahertz wave applied from the terahertz wave generation portion to an object to be measured, the terahertz wave being detected through the object to be measured. Furthermore, a waveform shaping portion configured to shape a first answer signal with respect to the terahertz wave by using a signal acquired in the above-described terahertz wave detection portion, a measurement condition acquisition portion configured to acquire a first measurement condition, and an answer signal storage portion configured to store second answer signals associated with the measurement conditions are included.

Moreover, a selection portion configured to select the above-described second answer signal from the above-described answer signal storage portion by using the above-described first measurement condition and a signal processing portion configured to conduct deconvolution with respect to the above-described first answer signal on the basis of the above-described second answer signal are included. Here, in the selection of the second answer signal, an answer signal corresponding to a second measurement condition closest to the above-described first measurement condition may be selected.

According to this configuration, an inspection apparatus which can suppress or reduce changes in signal based on changes in inspection environment can be provided. Incidentally, detection of an applied terahertz wave through an object to be measured refers to detection of a terahertz wave, e.g., a transmitted wave or a reflected wave, which has been influenced by the object to be measured. This object to be measured includes a solid, a gas, and a liquid.

Detailed explanations will be provided below with reference to the drawings.

Figure 1:
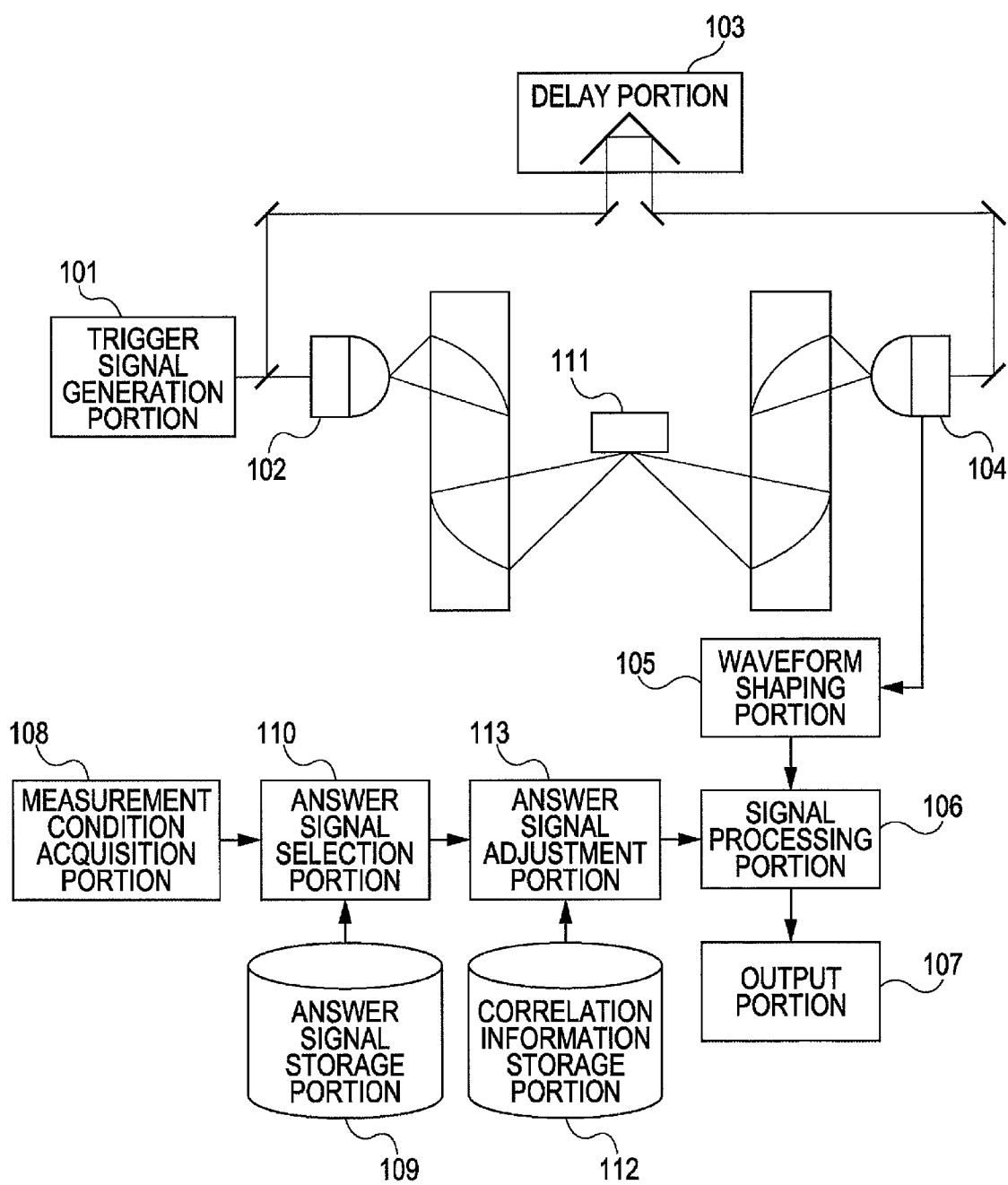
FIG. 1 is a schematic diagram for explaining the configuration of an inspection apparatus according to a first embodiment.

FIG. 1 is a schematic configuration diagram of a terahertz wave inspection apparatus according to the present embodiment. As shown in FIG. 1, the terahertz wave inspection apparatus according to the present embodiment has the following configuration.

The terahertz wave inspection apparatus is roughly divided into a section which forms a time waveform of a terahertz wave from an object to be measured 111 and a section which processes the time waveform of the resulting terahertz wave. The section which forms a time waveform of the terahertz wave is composed of a trigger signal generation portion 101, a terahertz wave generation portion 102, a delay portion 103, a terahertz wave detection portion 104, and a waveform shaping portion 105. The section which processes the time waveform of the terahertz wave is composed of a signal processing portion 106, an output portion 107, a measurement condition acquisition portion 108, an answer signal storage portion 109, an answer signal selection portion 110, a correlation information storage portion 112, and an answer signal adjustment portion 113.

The section which forms a time waveform of a terahertz wave performs operations to apply a pulsed terahertz wave to the object to be measured 111 and detect a terahertz wave from the object to be measured 111. As for this series of operations, a so-called terahertz time domain spectroscopy (THz-TDS) can be applied. The operations of individual portions will be described simply.

The trigger signal generation portion 101 generates a trigger signal for operating the terahertz wave generation portion 102 and the terahertz wave detection portion 104 described later. The trigger signal is a signal for operating devices constituting the terahertz wave generation portion 102 and the terahertz wave detection portion 104. Therefore, the types and the characteristics of the trigger signal are selected appropriately in accordance with the operation principle of the devices. The types of the trigger signal include optical signals and electric signals. For example, as for the optical signal, a signal which operates photoelectric conversion devices, e.g., a photodiode, can be applied. As for the electric signal, a signal which operates semiconductor devices, e.g., a transistor, can be applied. Furthermore, a transistor-transistor Logic (TTL) signal which drives a system can be applied. In the present invention, this trigger signal has an intermittent or periodic characteristic.

The terahertz wave generation portion 102 is a portion which generates a terahertz wave on the basis of the above-described trigger signal. The time waveform of the terahertz wave is in the shape of a pulse. As for the technique to generate such a terahertz wave, various techniques can be applied. Examples of these techniques include techniques which take advantage of an instantaneous carrying current and techniques which take advantage of a gain structure. As for the techniques which take advantage of an instantaneous carrying current, a technique to generate a terahertz wave from a surface of a mirror-polished semiconductor or an organic crystal and a photoconductive element in which an antenna pattern is formed on a semiconductor thin film from a metal electrode can be applied. Furthermore, a PIN diode can be applied. As for the techniques which take advantage of a gain structure, a technique by using a semiconductor quantum well structure can be applied.

The delay portion 103 is a portion for adjusting a delay time of a trigger signal which reaches the terahertz wave detection portion 104 relative to a trigger signal which reaches the terahertz wave generation portion 102. The adjustment of the delay time includes a technique to adjust an optical length directly and a technique to adjust an effective optical length. Examples of the direct adjustment techniques include a method by using a folding optical system and an operation portion. Examples of the technique to adjust an effective optical length include a method in which the time constant in a propagation path of a trigger signal is changed.

The terahertz wave detection portion 104 is a portion for detecting a terahertz wave by the trigger signal with a delay time adjusted in the delay portion 103. A semiconductor device which responds to a terahertz wave at real time has not yet been seen to be commercialized. Therefore, in THz-TDS, a momentary intensity signal of a terahertz wave at the point in time when a trigger signal is input is acquired, and a time waveform of the terahertz wave is sampled by this trigger signal. Examples of techniques associated with such a terahertz wave detection portion 104 include a technique to detect a current corresponding to a field intensity due to photoconduction, a technique to detect an electric field by using an electro-optic effect, and a technique to detect a magnetic field by using a magneto-optical effect. As for the technique to detect a current due to photoconduction, a photoconductive element can be applied. As for the technique to detect an electric field by using an electro-optic effect, a technique by using an orthogonal polarizer and an electro-optic crystal can be applied. As for the technique to detect a magnetic field by using a magneto-optical effect, a technique by using an orthogonal polarizer and a magneto-optical crystal can be applied.

The waveform shaping portion 105 is a portion for forming a time waveform of the terahertz wave from the momentary signal detected in the terahertz wave detection portion 104. In the present invention, the time waveform of the terahertz wave acquired in the waveform shaping portion 105 may also be referred to as a first answer signal.

Regarding the above-described section which forms a time waveform of a terahertz wave, the element configurations of the terahertz wave generation portion 102 and the terahertz wave detection portion 104 and arrangement of the optical system including them may be set optionally insofar as the time waveform of the terahertz wave from the object to be measured 111 can be acquired.

The section which processes the time waveform of the resulting terahertz wave will be described below. The operations of individual portions will also be described.

The signal processing portion 106 is a portion for conducting deconvolution with respect to the first answer signal on the basis of the second answer signal described later. When the first answer signal is assumed to be y(t) and the second answer signal is assumed to be h(t), the signal processing portion 106 computes a signal x(t) from the first answer signal y(t) by reducing the influence of the second answer signal h(t) on the basis of Formula (1) described below. From another point of view, the first answer signal y(t) from the object to be measured 111, which is acquired in the waveform shaping portion 105, is defined as a signal produced by changing the signal x(t) with the second answer signal h(t).

$$y(t) = \int_{-\infty}^{\infty} x(t)h(t-\tau)d\tau = x(t) * h(t) \quad \text{Formula (1)}$$

In Formula (1), the second answer signal h(t) is one signal. However, in some cases, a plurality of signals may be included. In this case, the first answer signal y(t) is defined as a signal produced by changing the signal x(t) with a plurality of factors, as represented by Formula (2).

$$y(t) = x(t) * h_1(t) * h_2(t) * \ldots * h_n(t)$$

(where n represents an integer) Formula (2)

The output portion 107 is a portion corresponding to a user interface and processes the computation result x(t) of the signal processing portion 106 appropriately so as to provide to a user. In some cases, the output portion 107 controls the operations of other units through the use of the computation result.

The measurement condition acquisition portion 108 is a portion for acquiring the measurement condition (first measurement condition) of the present inspection apparatus. The measurement condition is the information capable of changing the first answer signal from the object to be measured 111. Examples of the measurement condition include a measurement environment of the terahertz wave inspection apparatus, the information related to the properties of the object to be measured 111, and the information related to the structure of the object to be measured 111. Examples of the measurement environment of the terahertz wave inspection apparatus include a temperature, a humidity, and a fluctuation in power of the terahertz wave generation portion 102. Examples of the information related to the properties include the refractive index and the refractive index distribution of the object to be measured 111, the mixing ratio, the distribution properties, e.g., electrical conductivity, and the dispersion state of the mixture. Examples of the information related to the structure include the inside structure of the object to be measured 111, the structure being estimated on the basis of the production process and the product condition.

The answer signal storage portion 109 is a portion in which the second answer signals under predetermined measurement conditions (second measurement condition) are stored.

The answer signal selection portion 110 is a portion for acquiring the second answer signal stored in the answer signal storage portion 109 while referring to the first measurement condition acquired in the measurement condition acquisition portion 108. Specifically, the answer signal selection portion 110 selects the second measurement condition closest to the first measurement condition referred to and acquires a second answer signal corresponding to the second measurement condition. In the case where the first measurement condition is one type, the second measurement condition closest to the first measurement condition of interest is selected, and the second answer signal is acquired. In the case where a plurality of types of first measurement conditions are present, selection is conducted by using matrix tables with respect to multiple items. In the case where the second answer signal is acquired by using matrix tables with respect to multiple items, the answer signal selection portion 110 assigns weights to items with respect to a plurality of first measurement conditions and selects the second measurement condition closest to the first measurement condition with respect to individual items. Then, the answer signal selection portion 110 acquires the second answer signal from the matrix table. Furthermore, as described above, in the case where a plurality of types of first measurement conditions are present, it is assumed that the first answer signal is composed of a plurality of factors, and the second measurement conditions closest to the first measurement condition are acquired sequentially, so that the second answer signals corresponding to the second measurement conditions are acquired. In this case, the signal processing portion 106 conducts deconvolution with respect to the first answer signal on the basis of the plurality of second answer signals sequentially.

The correlation information storage portion 112 and the answer signal adjustment portion 113 described in FIG. 1 are disposed if necessary and are not indispensable in the present invention.

In the case where the correlation information storage portion 112 and the answer signal adjustment portion 113 are used, the following application forms are included.

Figure 15A:
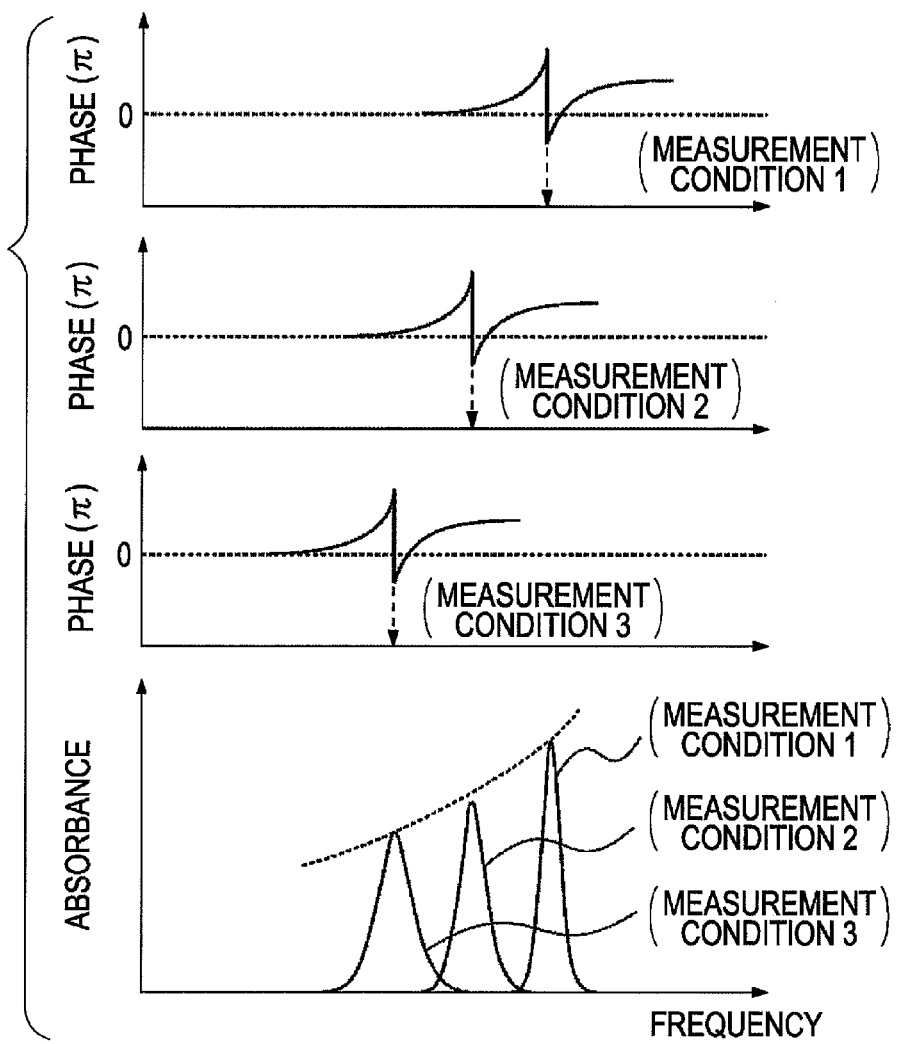
FIGS. 15A and 15B are diagrams for explaining correlation information.

Specifically, the above-described second answer signal extracted from the above-described answer signal storage portion 109 is fine-adjusted by these correlation information storage portion 112 and the answer signal adjustment portion 113, and the fine-adjusted signal is provided as the second answer signal to the signal processing portion 106. The second answer signals stored in the answer signal storage portion 109 are associated with the second measurement conditions. These second answer signals can be essentially associated with all measurement conditions which may be employed as the first measurement conditions. However, in some practical cases, discrete second measurement conditions are associated with the measurement conditions. The term "all measurement conditions" used here is defined as the state in which the second answer signals associated with the adjacent second measurement conditions become the same signal. That is, the state in which the second answer signals can be assigned to all first measurement conditions inclusively is referred to. Furthermore, discrete measurement conditions are defined as the state in which the second answer signals associated with the adjacent second measurement conditions are different. FIG. 15A shows an example in which second answer signals are associated with discrete second measurement conditions. FIG. 15A shows the absorbance and the state of phase on a measurement condition basis with respect to the second answer signals. The frequency characteristics of the plurality of second measurement conditions (measurement condition 1 to measurement condition 3) are different from each other.

The correlation information storage portion 112 is a portion in which the correlation information of the second answer signals stored in the answer signal storage portion 109 is defined and stored. The correlation information storage portion 112 has a function of predicting a second answer signal under the first measurement condition on the basis of the plurality of second answer signals.

Examples of the prediction techniques include a technique for predicting the tendency from second answer signals associated with measurement conditions (corresponding to the second measurement conditions stored in the answer signal storage portion 109) in the periphery of the first measurement condition and a technique in which a second answer signal under the first measurement condition is determined by calculation.

Figure 15B:
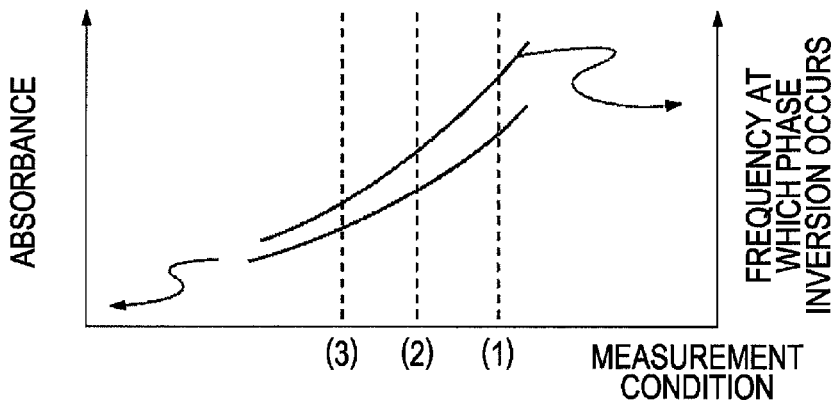

Examples of the technique to predict the tendency include a technique in which, as shown in FIG. 15B, prediction is conducted by drawing a calibration curve with respect to characteristic points of the second answer signals. As for the technique to determine by calculation, a technique to determine a change of the stored second answer signals by using relational expressions and simulations with respect to the measurement conditions in combination is conceived.

The answer signal adjustment portion 113 is a portion for fine-adjusting the second answer signal acquired in the answer signal selection portion 110 on the basis of the correlation information stored in the correlation information storage portion 112 in such a way as to meet the first measurement condition. For example, in the case where the correlation information is provided by the calibration curves as shown in FIG. 15B, the absorbance value, the frequency, and the frequency at which phase inversion occurs are fine-adjusted along these calibration curves. The answer signal adjustment portion 113 provides this fine-adjusted second answer signal to the signal processing portion 106. As described above, in the present invention, the correlation information storage portion 112 and the answer signal adjustment portion 113 are disposed as necessary.

The operation of the terahertz wave inspection apparatus will be described below.

The object to be measured 111 is arranged at a position at which the inspection is conducted. This arrangement method includes cases where the object to be measured 111 is moved and cases where the inspection apparatus is moved. The cases where the object to be measured 111 is moved include a case where a position and an orientation are controlled and a case where a plurality of objects to be measured 111 are moved to a predetermined place sequentially by a conveying mechanism, e.g., a belt conveyer. Furthermore, the cases where the inspection apparatus is moved include a case where an emission direction of a terahertz wave is changed by a driving mechanism and a case where a part of or a whole inspection apparatus is moved to a predetermined position.

The terahertz wave inspection apparatus starts an observation of a waveform of a terahertz wave, and the waveform shaping portion 105 forms a time waveform of the terahertz wave from the object to be measured 111 (first answer signal). The measurement condition acquisition portion 108 monitors the measurement condition in the observation of the waveform of the terahertz wave (first measurement condition). The answer signal selection portion 110 selects a measurement condition closest to the first measurement condition from the plurality of measurement conditions stored in the answer signal storage portion 109 (second measurement condition). Subsequently, the answer signal selection portion 110 acquire an answer signal corresponding to the second measurement condition (second answer signal). Computation can be conducted by directly using the answer signal acquired here.

Alternatively, in the answer signal adjustment portion 113, an amount of adjustment of the second answer signal to meet the second measurement condition to the first measurement condition is determined by using the correlation information stored in the correlation information storage portion 112. The answer signal adjustment portion 113 fine-adjusts the second answer signal by using the resulting amount of adjustment. Then, it is also possible that computation is conducted in the above-described signal processing portion 106 by using the resulting fine-adjusted answer signal.

Here, the computation is conducted in the signal processing portion 106 and refers to conduction of deconvolution with respect to the first answer signal on the basis of the second answer signal. The output portion 107 provides the computation result to a user, and the terahertz wave inspection apparatus finishes the inspection of the object to be measured 111.

As described above, in the present embodiment, even if the measurement condition is changed with time, the second answer signal is fine-adjusted following the change. As a result, regarding the computation result, the influence of the secular change on the measurement condition is suppressed. Consequently, according to the terahertz wave inspection apparatus of an embodiment of the present invention, even when the terahertz wave inspection apparatus is operated for a long time, it is possible to compensate changes in the measurement condition and enhance the versatility of the terahertz wave inspection apparatus.

Second Embodiment: Inspection Method

An inspection method using a terahertz wave according to the second aspect of the present invention includes the following steps.

Specifically, a step 1 is included, in which a waveform serving as a first answer signal is shaped by detecting the terahertz wave applied to an object to be measured, the terahertz wave being detected through the object to be measured. Furthermore, a step 2 is included, in which a measurement condition is acquired, and deconvolution with respect to the above-described first answer signal is conducted by using a second answer signal corresponding to the above-described acquired measurement condition. The above-described step 1 is executed by using, for example, the terahertz wave detection portion 104 and the waveform shaping portion 105 explained in the above-described first embodiment. The above-described step 2 is executed by, for example, the above-described measurement condition acquisition portion 108, the answer signal storage portion 109, the answer signal selection portion 110, and the signal processing portion 106.

As a matter of course, it is also possible that the above-described second answer signal is adjusted in accordance with the above-described measurement condition and, thereafter, the above-described deconvolution is conducted.

The inspection method according to the present embodiment is explained in detail in Example 1 described later.

Third Embodiment: Comparative Inspection Apparatus

The present embodiment shows one form of the terahertz wave inspection apparatus according to the present invention. Specifically, the present embodiment relates to a modified example of the above-described terahertz wave inspection apparatus. Explanations of the same parts as those described above will not be provided.

Figure 6:
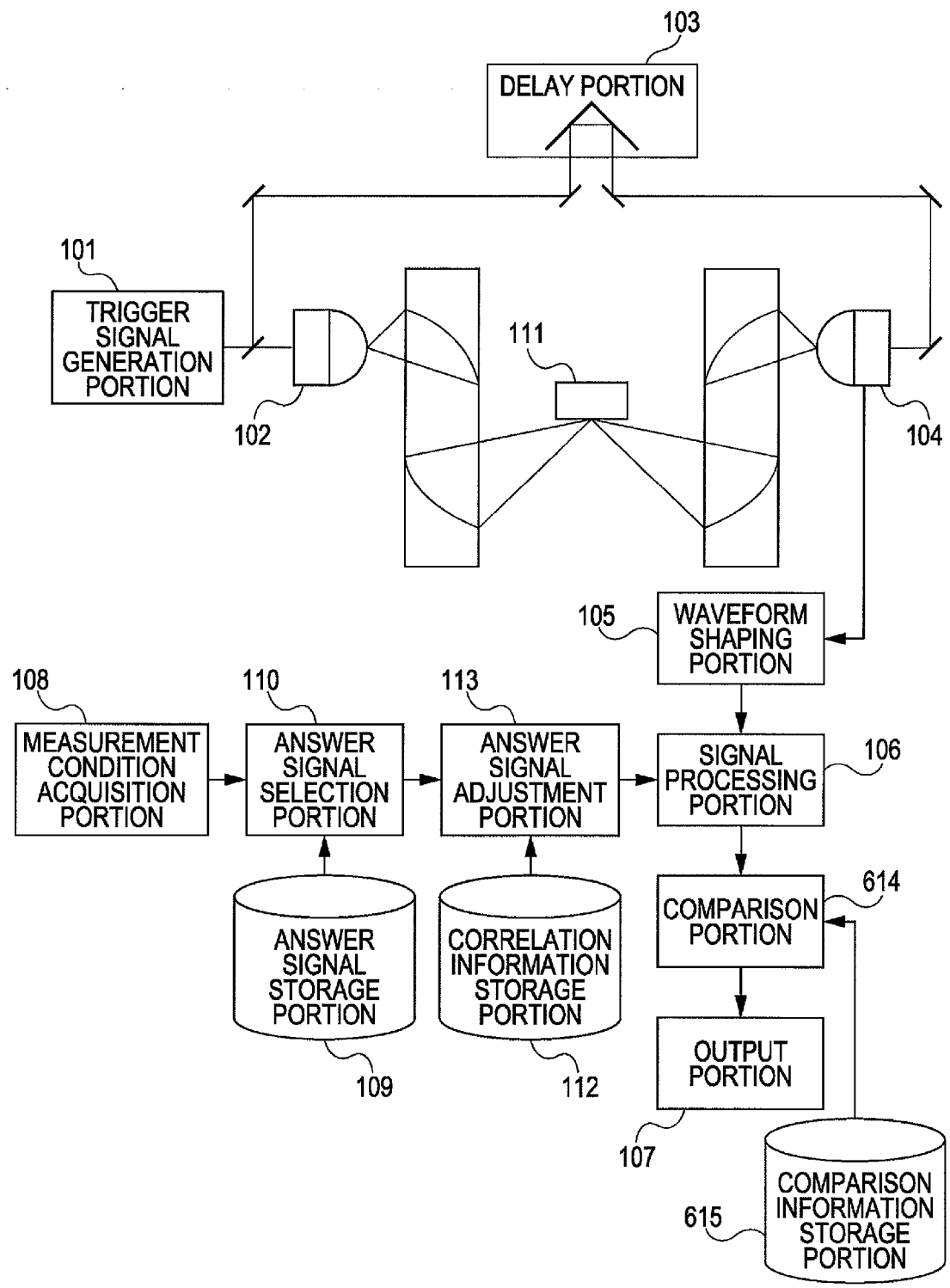
FIG. 6 is a diagram for explaining the configuration of a comparison apparatus according to a third embodiment.

FIG. 6 is a schematic configuration diagram of a terahertz wave inspection apparatus according to the present embodiment. As shown in FIG. 6, the terahertz wave inspection apparatus according to the present embodiment includes a section which forms a time waveform of a terahertz wave from the above-described object to be measured 111 and a section which processes the time waveform of the resulting terahertz wave. In addition to these configurations, the terahertz wave inspection apparatus includes a comparison portion 614 and a comparison information storage portion 615.

The operations of individual portions will be described simply.

The comparison portion 614 is a portion for comparing the computation result of the signal processing portion 106 and the information of the comparison information storage portion 615 described later. Examples of the comparison methods in the comparison portion 614 include a method in which extents relative to some reference value are compared and a method in which shapes are compared. For example, in the case where extents relative to some reference value are compared, a method in which comparison is made on the basis of whether or not a total amount and an average value of intensity exceed reference values is included. Furthermore, a method regarding the waveform of the computation result in the signal processing portion 106, in which comparison is made on the basis of whether or not there is a part (for example, intensity and inclination) exceeding the reference is included. In the case where the shapes are compared, a method in which comparison is made on the basis of whether or not the waveforms of the computation results in the signal processing portion 106 are equal is included. At this time, even when conformity is not perfect, a method in which comparison is made on the basis of whether or not nonconformity is within a predetermined range is also included. Moreover, a method in which comparison is made on the basis of whether or not a characteristic shape of the waveform is present is included. These comparisons are made in one of a time domain and a frequency domain.

The comparison information storage portion 615 is a portion for providing information used in the above-described comparison methods. This information is defined by the user.

The operations of the terahertz wave inspection apparatus according to the present embodiment will be described below. Explanations of the same operations as those described above will not be provided.

The terahertz wave inspection apparatus according to the present embodiment inspects a difference from an ideal state with respect to the object to be measured 111. Therefore, the answer signal storage portion 109 stores answer signals in the ideal state of the object to be measured 111 (second answer signal). Here, the ideal state of the object to be measured 111 is determined on the basis of the measurement environment of the above-described inspection apparatus assumed by the user and the information related to the properties and the information related to the structure of the object to be measured 111. That is, the terahertz wave inspection apparatus according to the present embodiment inspects situations, e.g., inclusion of foreign substances into the inside of the object to be measured 111, which are not assumed by the user. In the case where the above-described information related to the ideal state of the object to be measured is provided in the above-described comparison information storage portion, the difference from the above-described ideal state of the object to be measured is made clear by conducting comparison between the computation result in the above-described signal processing portion 106 and the information in the comparison portion.

The answer signal adjustment portion 113 fine-adjusts the second answer signal in such a way as to meet the first measurement condition of the measurement condition acquisition portion 108. The signal processing portion 106 conducts deconvolution with respect to the first answer signal on the basis of the second answer signal. The comparison portion 614 compares computation results and makes a judgment on the basis of the judgment criteria stored in the comparison information storage portion 615. The output portion 107 provides the comparison result to the user, and the terahertz wave inspection apparatus finishes the inspection of the object to be measured 111.

In the case where the waveform shaping portion 105 and the answer signal adjustment portion 113 input the same signal to the signal processing portion 106, the output of the signal processing portion 106 approximates a delta function. This state indicates the actual measurement result and the result estimated from the measurement condition are equal. Therefore, the object to be measured 111 can be considered to be in the ideal state assumed by the user. The average intensity on a time base of the delta function becomes substantially a level of noise. For example, if a foreign substance is included in the inside of the object to be measured 111, as described above, the output result of the signal processing portion 106 does not become a delta function. That is, the average intensity on the time base of the delta function becomes an eigenvalue at a level of noise or more. It becomes possible to increase a signal ratio by comparing the resulting signal with the result of deconvolution, and the reliability of the inspection can be improved. In this manner, according to the present embodiment of the invention, the output of the ideal state can be approximated to the delta function. Consequently, the signal intensity on a frequency basis becomes substantially a level of noise. It becomes possible to increase a signal ratio by comparing the resulting signal with the result of deconvolution and, therefore, the reliability of the inspection can be improved.

In the present embodiment according to the invention, as in the above-described first embodiment, the correlation information storage portion 112 and the answer signal adjustment portion 113 shown in FIG. 6 are used as necessary.

Fourth Embodiment: Imaging Inspection Apparatus

The present embodiment shows one form of the terahertz wave inspection apparatus according to the present invention. Specifically, the present embodiment relates to a modified example of the above-described terahertz wave inspection apparatus. Explanations of the same parts as those described above will not be provided.

Figure 9:
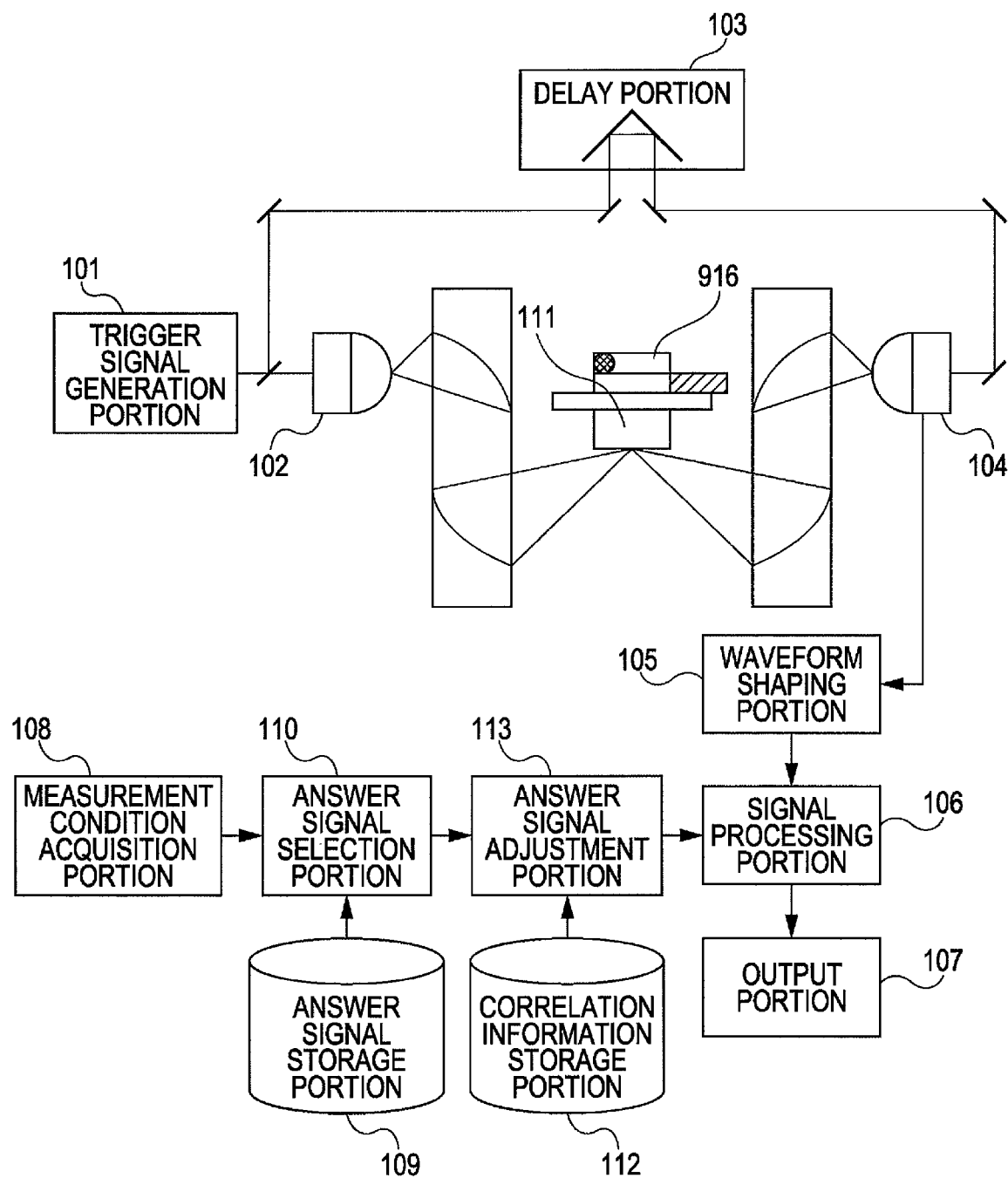
FIG. 9 is a schematic diagram for explaining the configuration of a comparison inspection apparatus according to a fourth embodiment.

FIG. 9 is a schematic configuration diagram of a terahertz wave inspection apparatus according to the present embodiment. As shown in FIG. 9, the terahertz wave inspection apparatus according to the present embodiment includes a section which forms a time waveform of a terahertz wave from the above-described object to be measured 111 and a section which processes the time waveform of the resulting terahertz wave. In addition to these configurations, the terahertz wave inspection apparatus according to the present embodiment includes a stage 916.

The operations of individual portions will be described simply.

The stage 916 is a stage which moves a position of application of the terahertz wave to the object to be measured 111 relatively. The stage 916 moves the position of application of the terahertz wave to the object to be measured 111 in a linear direction, a planar direction, and a direction in combination of these directions and a depth direction. In FIG. 9, the linear direction refers to a direction in which the position of application is moved linearly in a plane perpendicular to the drawing. The planar direction refers to a direction in which the position of application is moved in a plane perpendicular to the drawing. The depth direction refers to a direction in which the position of application is moved in a plane parallel to the drawing.

The operations of the terahertz wave inspection apparatus according to the present embodiment will be described below. Explanations of the same operations as those described above will not be provided.

The object to be measured 111 is placed on the stage 916. When a measurement is started, the stage 916 moves the object to be measured 111 to a predetermined position. The waveform shaping portion 105 forms a time waveform of the terahertz wave from the object to be measured 111 (first answer signal). The measurement condition acquisition portion 108 monitors the measurement condition during the observation of the waveform of the terahertz wave (first measurement condition). The answer signal adjustment portion 113 fine-adjusts the selected second answer signal in such a way as to meet the state of the first measurement condition. The signal processing portion 106 conducts deconvolution with respect to the first answer signal on the basis of the second answer signal.

The stage 916 moves the object to be measured 111 to a position of the next inspection, and the inspection is conducted again. When the inspection in a predetermined region is completed, the output portion 107 produces an image of the inspection result and provides it to the user.

Figure 13:
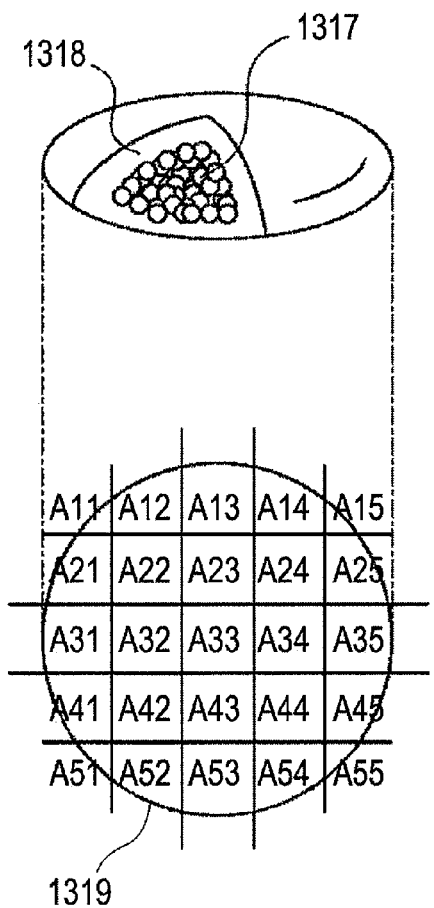
FIG. 13 is a diagram for explaining a method for assigning second answer signals.

Here, in the case where the information stored in the answer signal storage portion 109 (second answer signal) is the information of the object to be measured 111 itself, e.g., the information related to the properties of the object to be measured 111 and the information related to the structure of the object to be measured 111, the following forms can be employed. As shown in FIG. 13, the object to be measured 111 is divided into a plurality of inspection regions Aab (where a and b are integers), and a second answer signal is assigned to each region. According to such a configuration, the object to be measured 111 can be inspected in more detail. For example, a tablet (in which a powder 1317 is covered with a coating film 1318) shown in FIG. 13 is in the shape having a curved surface. Regarding such a shape, an influence of the change in shape exerted on the waveform of the terahertz wave can be suppressed by fine-defining the inspection regions as compared with that in the case where the second answer signal is assigned comprehensively to the whole shape. According to such a configuration, a fine-grained response can be given in accordance with changes in measurement condition characteristic to the object to be measured, e.g., changes in property distribution and shape. Consequently, the reliability of the inspection can be improved. As described above, an influence of secular change of the measurement condition during image acquisition can be suppressed by disposing the stage 916 which moves the position of application of the above-described terahertz wave to the above-described object to be measured relatively. Therefore, the effect that the versatility of the inspection apparatus can be improved is further exerted.

As shown in FIG. 13, it is also possible to set a plurality of inspection regions 1319 with respect to the above-described object to be measured and define the above-described second answer signal on an inspection region basis. In such a case, since a fine-grained response can be given in accordance with changes in measurement condition characteristic to the object to be measured, e.g., changes in property distribution and shape, an effect that the reliability of the inspection can be improved is exerted.

Figure 14A:
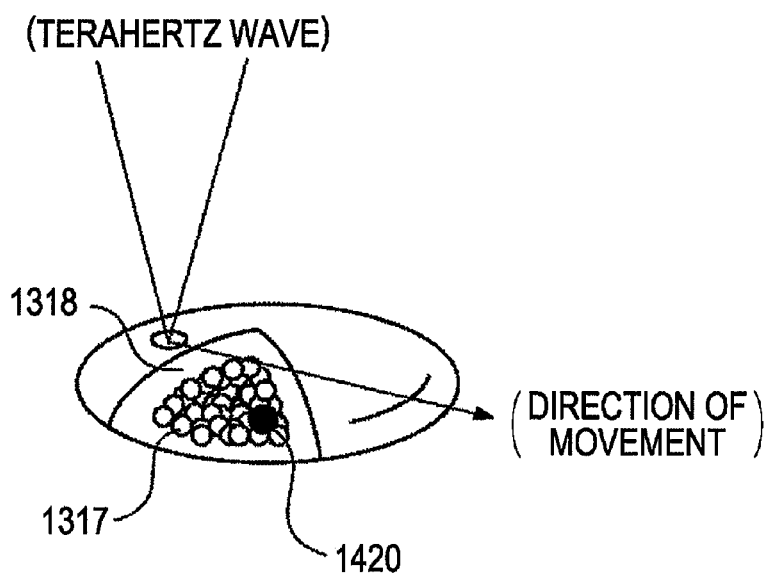
FIGS. 14A to 14C are diagrams for explaining an apparatus for inspecting a difference from an ideal state according to a third embodiment.
Figure 14B:
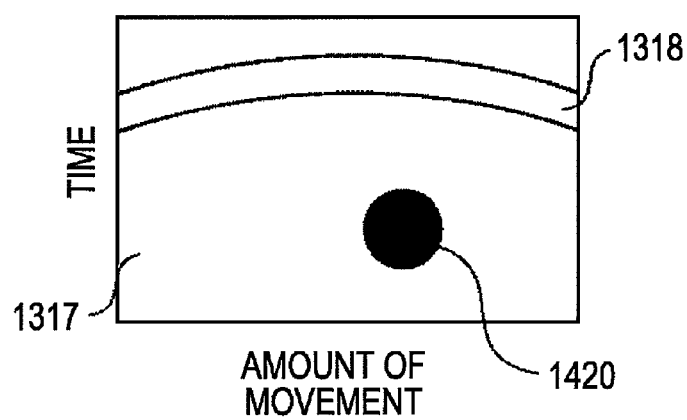
Figure 14C:
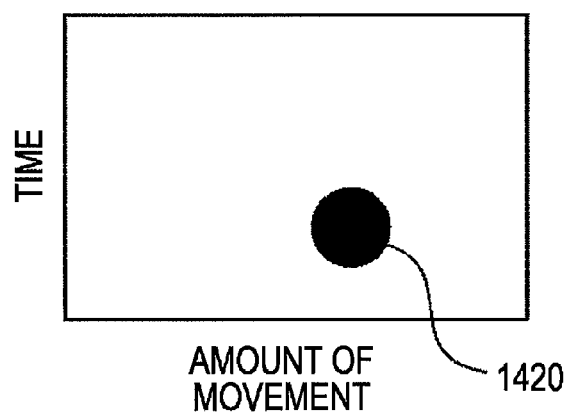

Furthermore, in the form in which a difference from an ideal state with respect to the object to be measured 111 is inspected, as shown in the third embodiment, the following inspection method can also be employed. In FIG. 14A, a state in which no foreign substance is present in the inside of the object to be measured 111 (here, a tablet) is assumed to be an ideal state. At this time, in a common imaging inspection, as shown in FIG. 14B, the internal structure of the object to be measured 111 including a foreign substance 1420 is provided from the output portion 107. At this time, in many cases, it is necessary that a user watching the image judges presence or absence of the foreign substance 1420. However, as described above, in the form in which a difference from an ideal state is inspected, it becomes possible that the image provided from the output portion 107 indicate a difference from the ideal state, i.e. only the foreign substance 1420, as shown in FIG. 14C. According to such a configuration, a load of judgment on the user can be reduced.

In this manner, the configuration of the present embodiment enables conduction of the imaging inspection. According to this configuration, an influence of secular change of the measurement condition during image acquisition can be suppressed and, therefore, the versatility of the inspection apparatus can be further improved.

In the present embodiment according to the invention, as in the above-described first embodiment, the correlation information storage portion 112 and the answer signal adjustment portion 113 shown in FIG. 6 are used as necessary.

EXAMPLES

Example 1

The present example relates to a terahertz wave inspection apparatus which suppresses a secular change in the measurement condition, shown in the first embodiment.

The object to be measured 111 is a mirror which perfectly reflects a terahertz wave. The measurement condition acquisition portion 108 monitors a temperature and a humidity during inspection. The answer signal storage portion 109 stores information of spectra of steam under predetermined environments (temperature and humidity).

Figure 2:
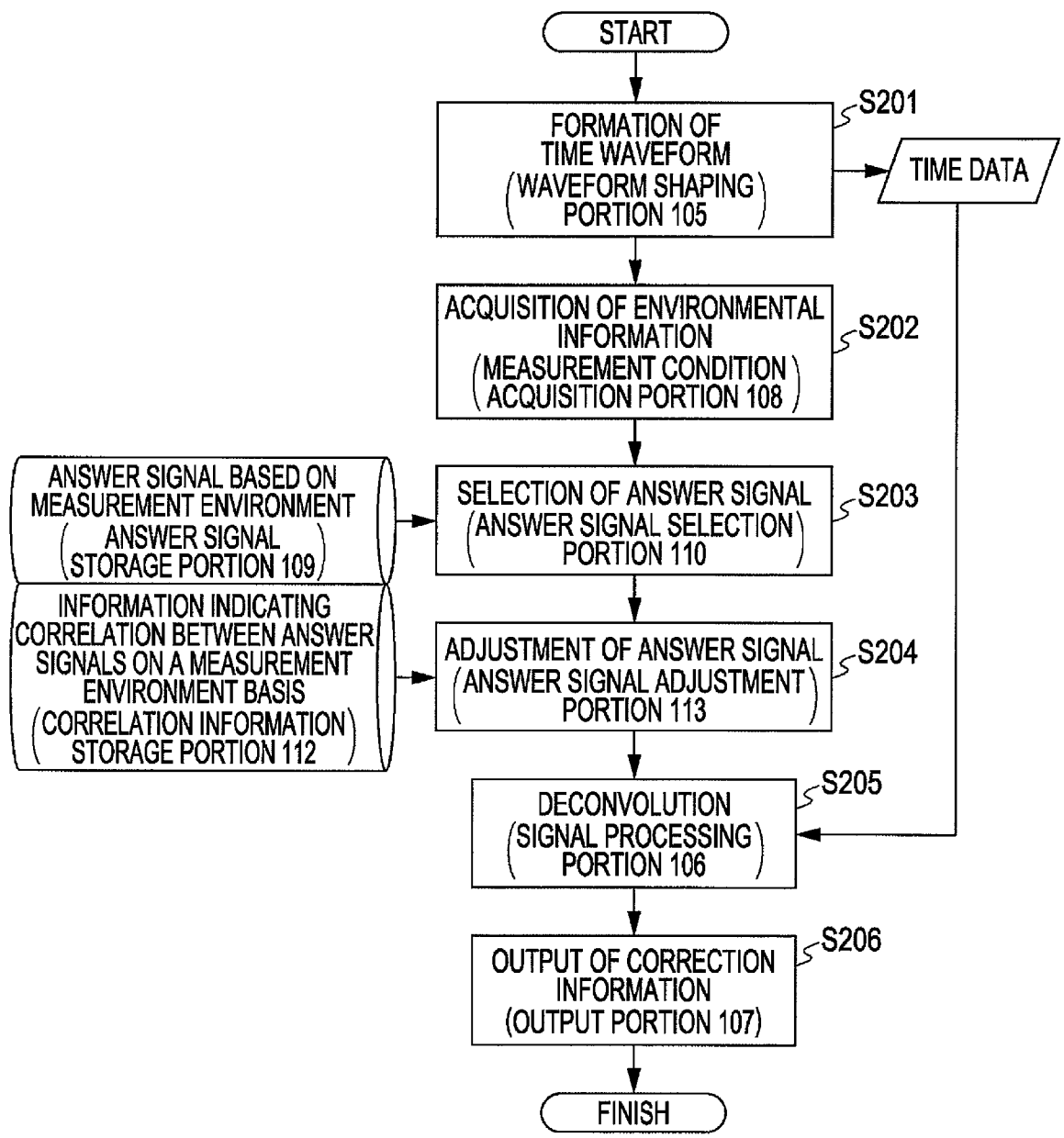
FIG. 2 is a flow diagram for explaining operations of an inspection apparatus according to an Example 1.
Figure 3A:
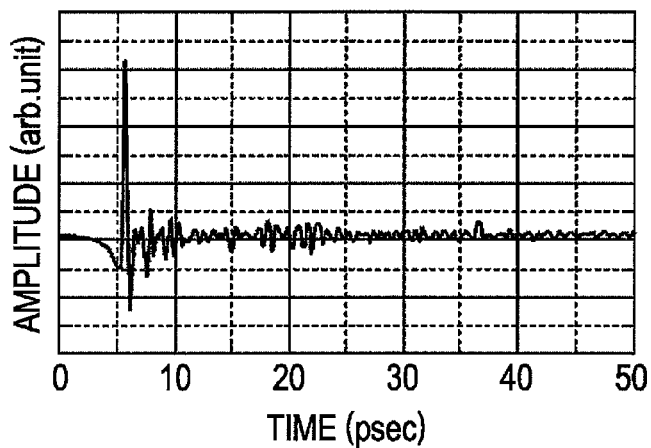
FIGS. 3A to 3C are diagrams showing waveforms of individual portions of the inspection apparatus according to Example 1.
Figure 3B:
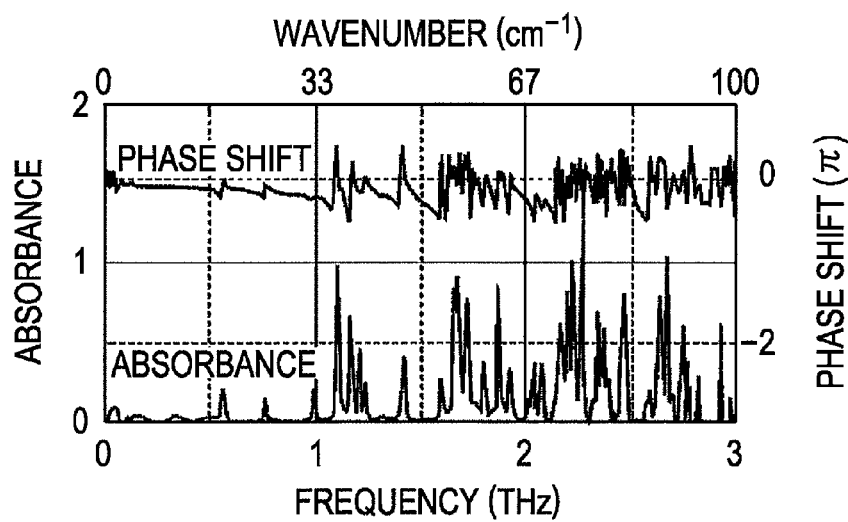
Figure 3C:
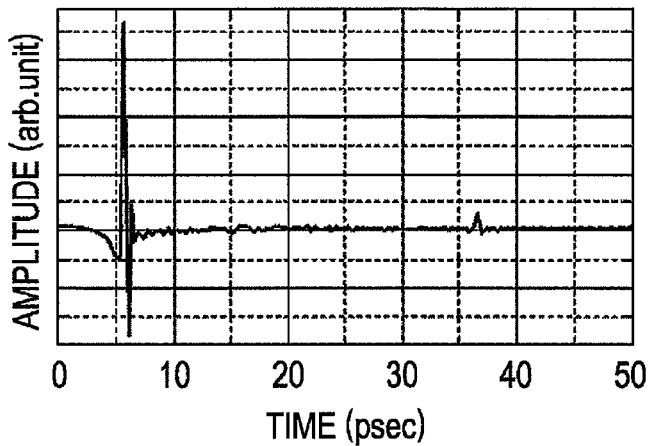

FIG. 2 is an operation flow diagram of the present terahertz wave inspection apparatus. As shown in FIG. 2, when the inspection is started, the waveform shaping portion 105 forms a time waveform of a terahertz wave (S201, first answer signal). The time waveform at this time is shown in FIG. 3A. As shown in FIG. 3A, a vibrational component of steam is superimposed on the time waveform of the terahertz wave. Subsequently, the measurement condition acquisition portion 108 monitors the temperature and the humidity during acquisition of time waveform (S202, first measurement condition). The answer signal selection portion 110 acquires an answer signal (second answer signal) under a measurement condition (second measurement condition) closest to the first measurement condition (S203). The second answer signal at this time is shown in FIG. 3B. The answer signal adjustment portion 113 fine-adjusts the intensity and the positions of peaks in such a way as to meet the first measurement condition (S204). The signal processing portion 106 conducts deconvolution with respect to the first answer signal on the basis of the second answer signal (S205). The computation result at this time is shown in FIG. 3C. As shown in FIG. 3C, the computation result is a time waveform in which an influence of steam is suppressed. The output portion 107 outputs the result of the above-described deconvolution (S206). Here, the above-described result refers to a time waveform which is the time waveform acquired in the waveform shaping portion 105 and corrected by suppressing a secular change in the measurement environment.

According to the present example, in the inspection of the object to be measured 111, the inspection can be conducted while an influence of steam in the air is suppressed. Therefore, a unit which has been previously necessary for adjusting the environment becomes unnecessary, and the inspection can be conducted in a free space. Since the unit for adjusting the environment is unnecessary, miniaturization and price reduction of the apparatus are facilitated. Furthermore, since the inspection can be conducted in a free space, the versatility of the apparatus of the present example can be improved.

Example 2

The present example relates to a terahertz wave inspection apparatus which suppresses a change in the component proportion ratio of substances in the inside of the object to be measured 111, shown in the first embodiment.

The object to be measured 111 is a pellet of a mixture of polyethylene and deoxycytidine hydrochloride (DCHCL). The measurement condition acquisition portion 108 monitors the amount of polyethylene. The amount of polyethylene is acquired from the usage before mixing. The answer signal storage portion 109 stores information of spectra of polyethylene under predetermined masses.

Figure 4:
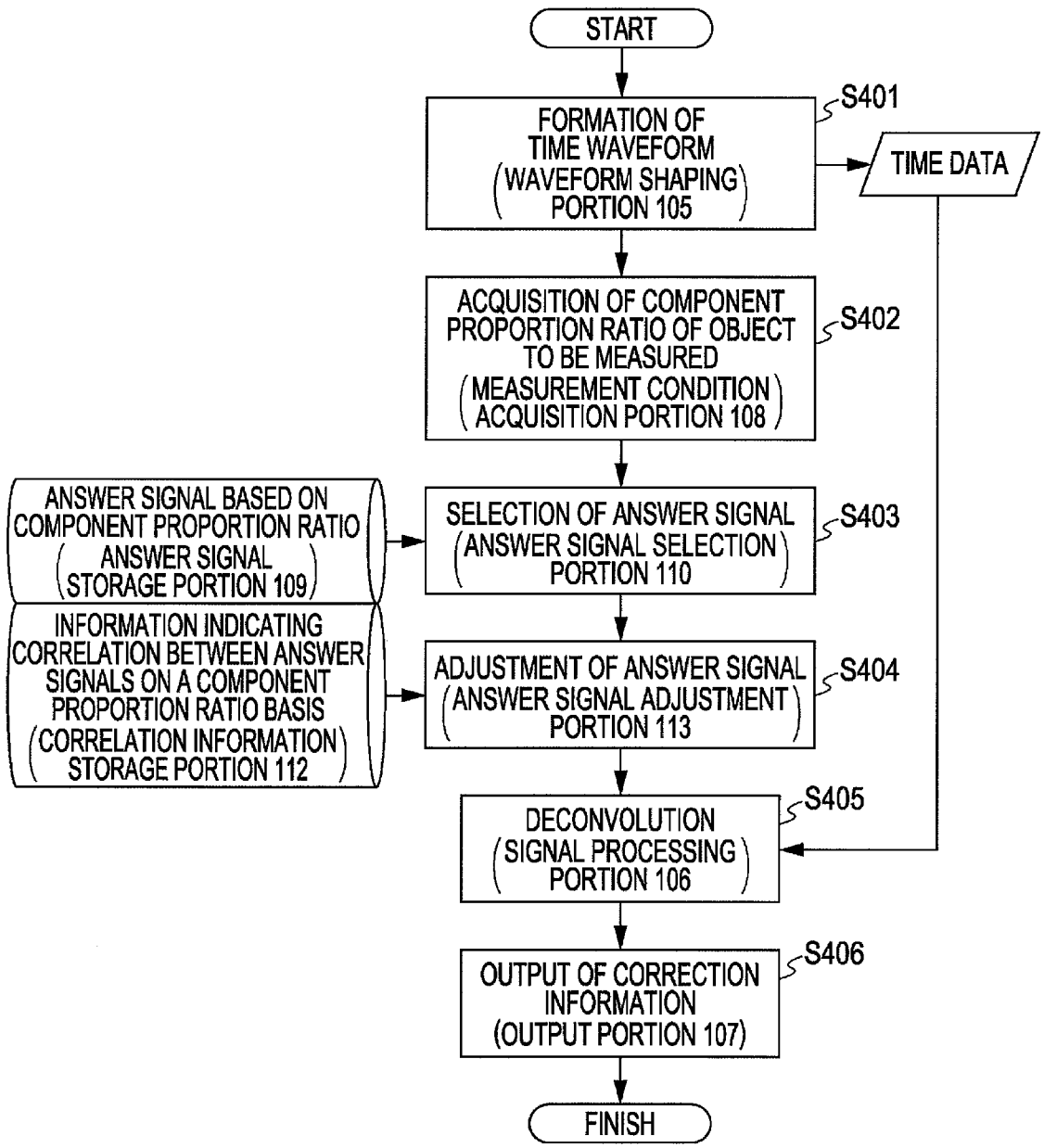
FIG. 4 is a flow diagram for explaining operations of an inspection apparatus according to an Example 2.
Figure 5A:
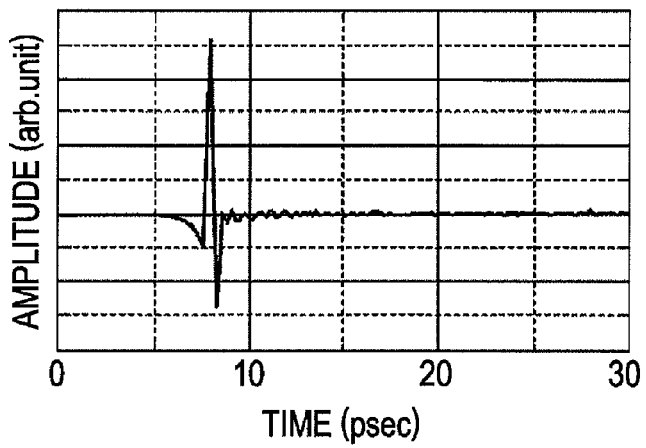
FIGS. 5A to 5C are diagrams showing waveforms of individual portions of the inspection apparatus according to Example 2.
Figure 5B:
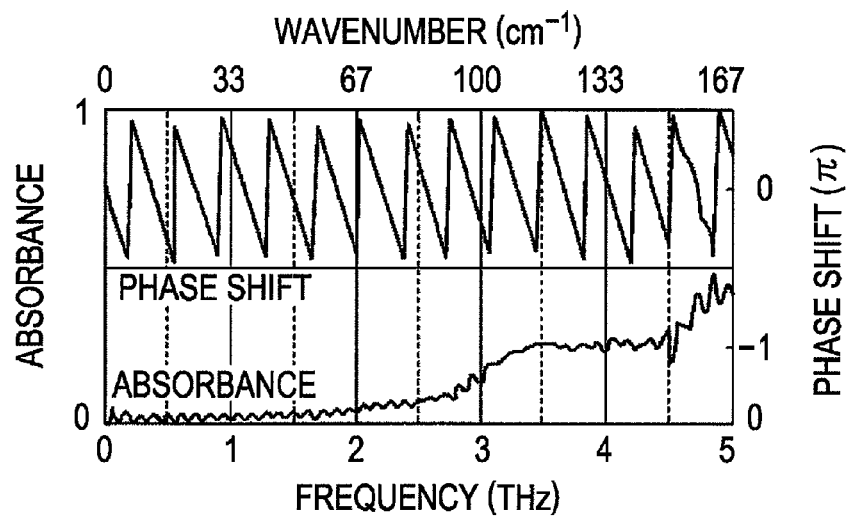
Figure 5C:
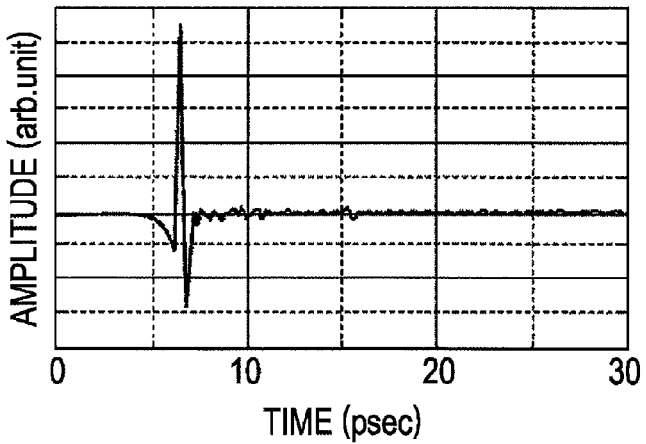

FIG. 4 is an operation flow diagram of the present terahertz wave inspection apparatus. As shown in FIG. 4, when the inspection is started, the waveform shaping portion 105 forms a time waveform of a terahertz wave (S401, first answer signal). The time waveform at this time is shown in FIG. 5A. In FIG. 5A, information of polyethylene and information of DCHCL are superimposed. Subsequently, the measurement condition acquisition portion 108 monitors the usage of polyethylene used for production of the pellet (S402, first measurement condition). When this usage is changed, the component proportion ratios of materials are changed. The answer signal selection portion 110 acquires an answer signal (second answer signal) under a measurement condition (second measurement condition) closest to the first measurement condition (S403). The second answer signal at this time is shown in FIG. 5B. The answer signal adjustment portion 113 fine-adjusts the intensity and the phase shown in FIG. 5B in such a way as to meet the first measurement condition (S404). The signal processing portion 106 conducts deconvolution with respect to the first answer signal on the basis of the second answer signal (S405). The computation result at this time is shown in FIG. 5C. As shown in FIG. 5C, the computation result is a time waveform in which an influence of polyethylene is suppressed, and the positions of occurrences of pulses and the intensity are changed. The output portion 107 outputs the result of the above-described deconvolution (S406). Here, the above-described result refers to a time waveform which is the time waveform acquired in the waveform shaping portion 105 and corrected by suppressing an influence of polyethylene.

According to the present example, in the inspection of the object to be measured 111, an influence of a specific substance is suppressed. Consequently, inspection of only a desired material can be conducted and, therefore, the versatility of the apparatus can be improved.

Example 3

The present example relates to a terahertz wave inspection apparatus which suppresses a secular structural change of the object to be measured 111 shown in the third embodiment and inspects a foreign substance in the inside of the object to be measured 111.

The object to be measured 111 is a photonic crystal in which the refractive index changes periodically. The measurement condition acquisition portion 108 monitors a process condition of a production process. The answer signal storage portion 109 stores information of spectra of the photonic crystal under predetermined process conditions.

Figure 7:
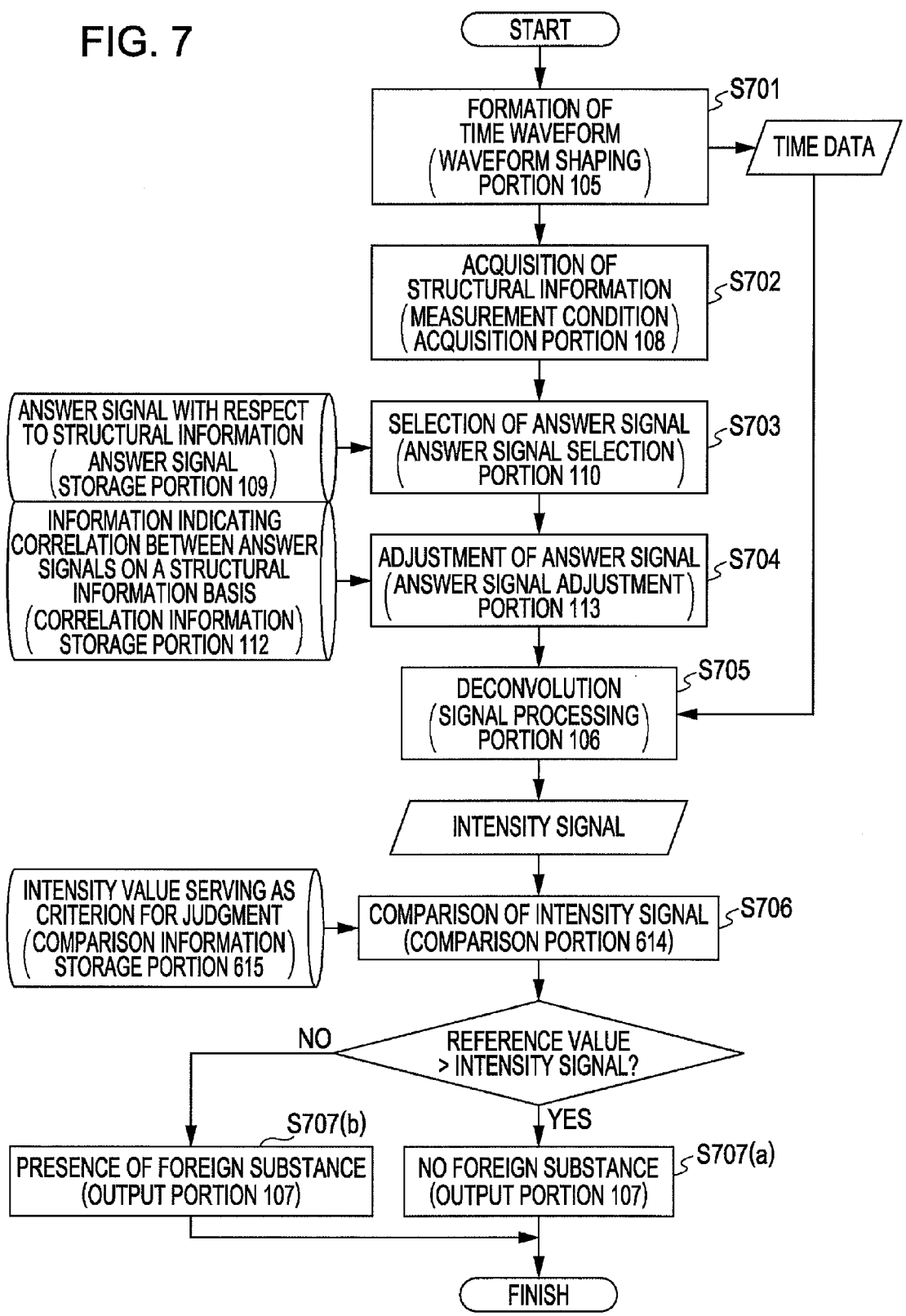
FIG. 7 is a flow diagram for explaining operations of the inspection apparatus according to an Example 3.

FIG. 7 is an operation flow diagram of the present terahertz wave inspection apparatus. As shown in FIG. 7, when the inspection is started, the waveform shaping portion 105 forms a time waveform of a terahertz wave (S701, first answer signal).

Figure 8A:
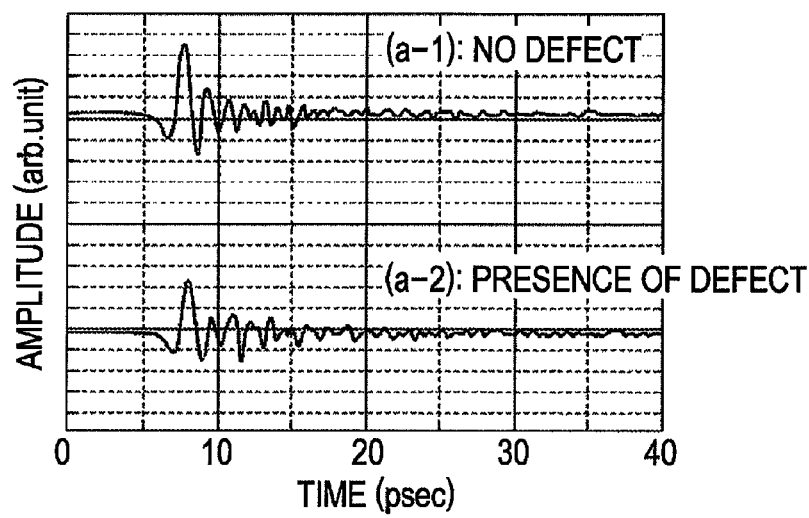
FIGS. 8A to 8C are diagrams showing waveforms of individual portions of the inspection apparatus according to Example 3.
Figure 8B:
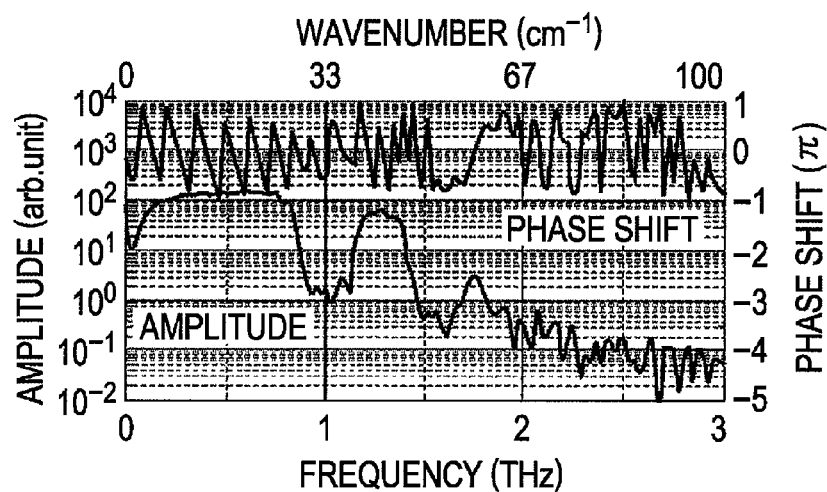
Figure 8C:
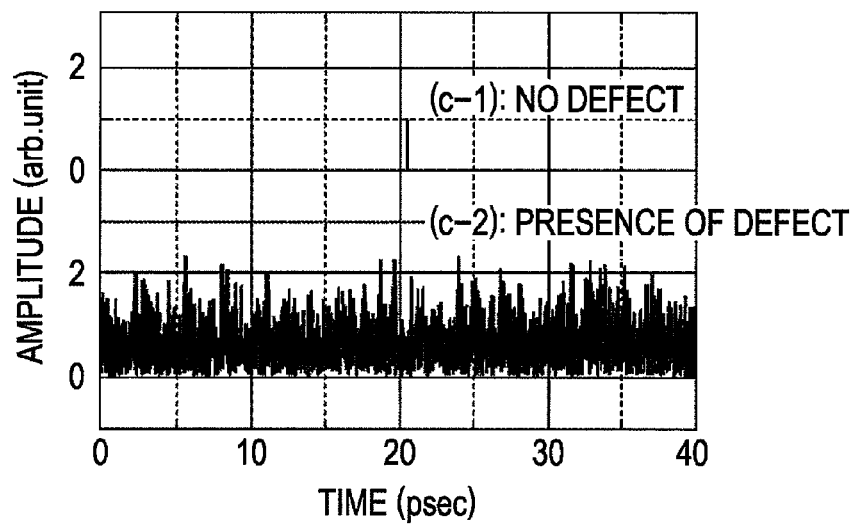

The time waveform at this time is shown in FIG. 8A. In FIG. 8A, a time waveform of the upper case (a-1) is a signal from a photonic crystal in which no defect is present, and a time waveform of the lower case (a-2) is a signal from a photonic crystal in which a defect is present (a part of a periodic structure is deformed). As shown in FIG. 8A, in these waveforms, a vibration component derived from a photonic band gap is present. Subsequently, the measurement condition acquisition portion 108 monitors a process condition in a photonic crystal production process (S702, first measurement condition). The answer signal selection portion 110 acquires an answer signal (second answer signal) under a measurement condition (second measurement condition) closest to the first measurement condition (S703). The second answer signal acquired at this time is information related to a structure predicted from the process condition. The second answer signal at this time is shown in FIG. 8B. The answer signal adjustment portion 113 fine-adjusts the position of the band end and the intensity in such a way as to meet the first measurement condition (S704). The signal processing portion 106 conducts deconvolution with respect to the first answer signal on the basis of the second answer signal (S705). The computation result at this time is shown in FIG. 8C. As shown in FIG. 8C, in the case where no defect is present in the structure of the photonic crystal, a signal in the shape of a delta function is output (FIG. 8C (c-1)), and in the case where a defect is present in the structure, a continuous signal is output (FIG. 8C (c-2)).

Next, regarding these signals, an average intensity signal is calculated. In the case where no defect is present, an average intensity of the waveform is 0.0005, and in the case where a defect is present, an average intensity is 0.6. The comparison information storage portion 615 sets an intensity signal serving as a predetermined reference. In the present example, the reference is set at 0.1. The comparison portion 614 conducts a comparison between an intensity value serving as a reference and the average intensity of the waveform shown in FIG. 8C (S706). When an average intensity based on the computation result is small as compared with the intensity value serving as the reference, it is judged that no foreign substance is present (S707(a)). On the other hand, when an average intensity based on the computation result is large as compared with the intensity value serving as the reference, it is judged that a foreign substance is present (S707(b)).

According to the present example, a ratio of a signal in the case where no foreign substance is present to a signal in the case where a foreign substance is present is three orders of magnitude or larger. Therefore, the foreign substance detection sensitivity can be improved easily.

Example 4

The present example relates to a terahertz wave inspection apparatus which suppresses a secular change in the measurement environment, shown in the fourth embodiment. In particular, the present example relates to an imaging inspection apparatus.

The object to be measured 111 is paper having a thickness of 90 µm. The measurement condition acquisition portion 108 monitors a temperature and a humidity during inspection. The answer signal storage portion 109 stores answer signals from a mirror perfectly reflecting the terahertz wave under predetermined environments (temperature and humidity).

Figure 10:
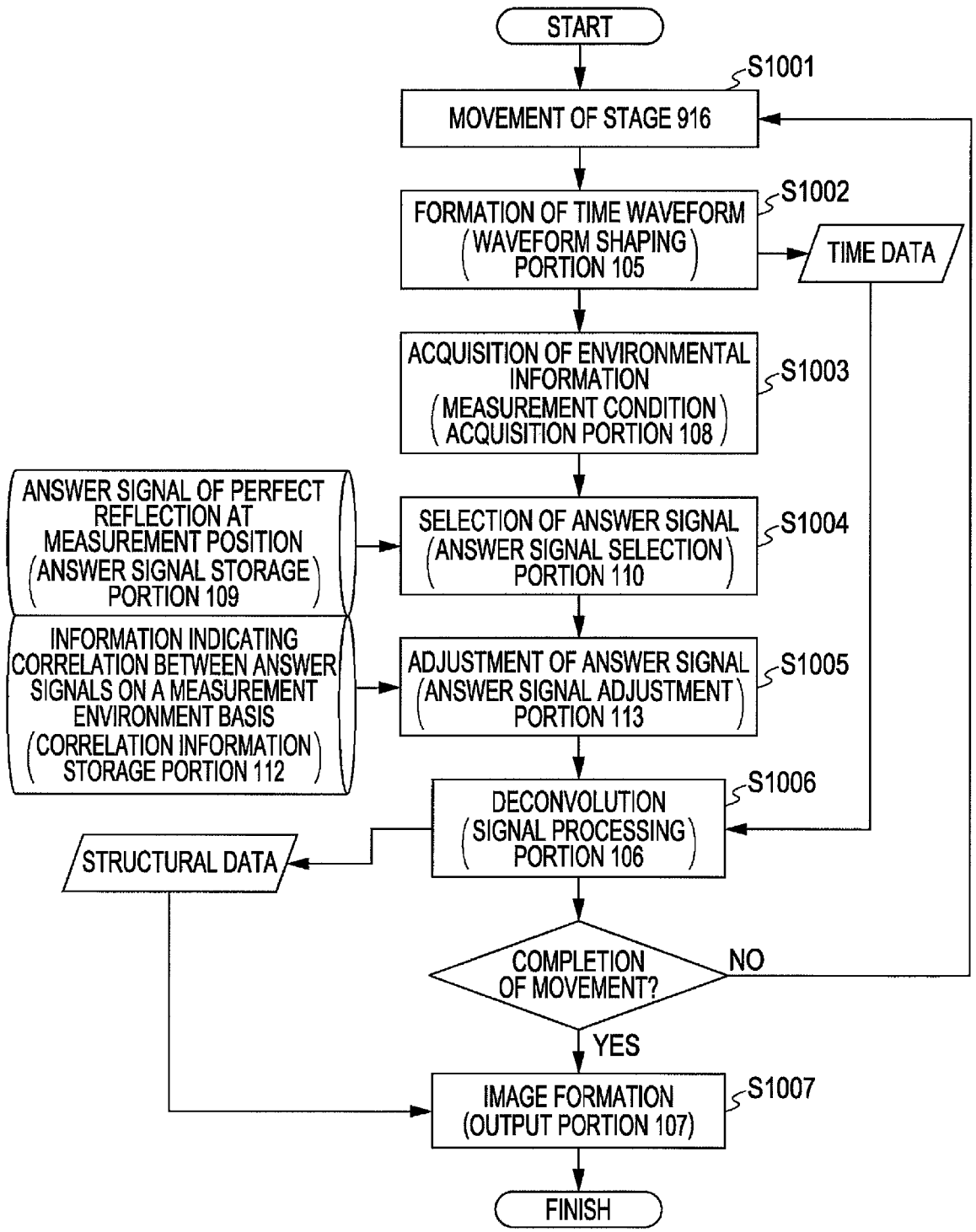
FIG. 10 is a flow diagram for explaining operations of the inspection apparatus according to an Example 4.
Figure 11A:
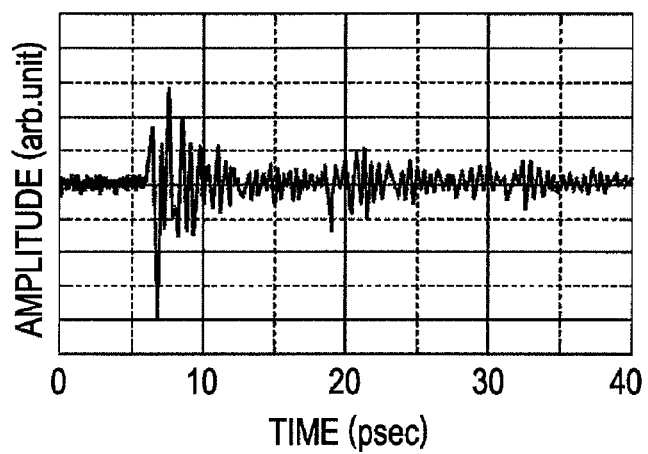
FIGS. 11A to 11C are diagrams showing waveforms of individual portions of the inspection apparatus according to Example 4.
Figure 11B:
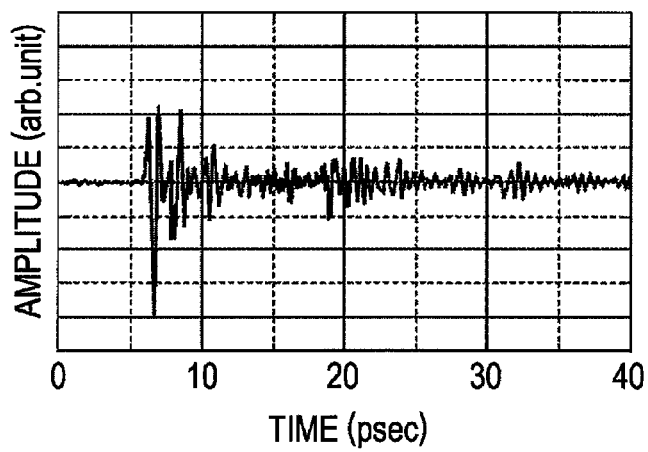
Figure 11C:
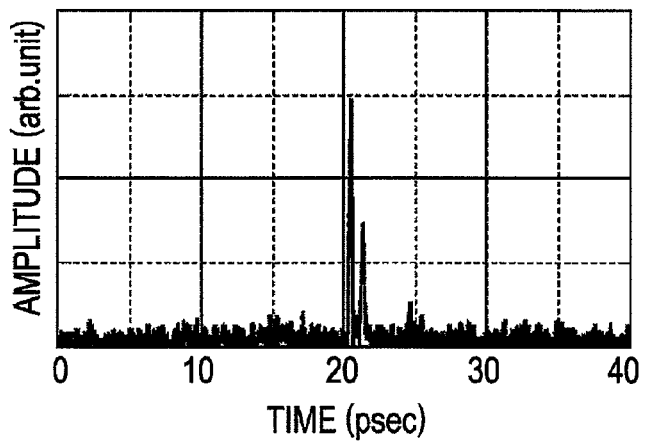

FIG. 10 is an operation flow diagram of the present terahertz wave inspection apparatus. As shown in FIG. 10, when the inspection is started, the stage 916 moves the object to be measured 111 to an inspection start point (S1001). The waveform shaping portion 105 forms a time waveform of a terahertz wave at the place after the movement (S1002, first answer signal). The time waveform at this time is shown in FIG. 11A. As shown in FIG. 11A, reflection at the interface of paper and a vibrational component of steam are superimposed on the time waveform of the terahertz wave. Subsequently, the measurement condition acquisition portion 108 monitors the temperature and the humidity during acquisition of time waveform (S1003, first measurement condition). The answer signal selection portion 110 acquires an answer signal (second answer signal) under a measurement condition (second measurement condition) closest to the first measurement condition (S1004). The second answer signal at this time is shown in FIG. 11B. The answer signal adjustment portion 113 Fourier-transforms the time waveform shown in FIG. 11B and fine-adjusts the intensity and peaks on a frequency axis in such a way as to meet the first measurement condition (S1005). The signal processing portion 106 conducts deconvolution with respect to the first answer signal on the basis of the second answer signal (S1006). The computation result at this time is shown in FIG. 11C. As shown in FIG. 11C, the computation result is a time waveform in which an influence of steam is suppressed and only a response from the reflection interface of the paper is reflected. Thereafter, the stage 916 moves the object to be measured 111 to a position of the next inspection.

Figure 12:
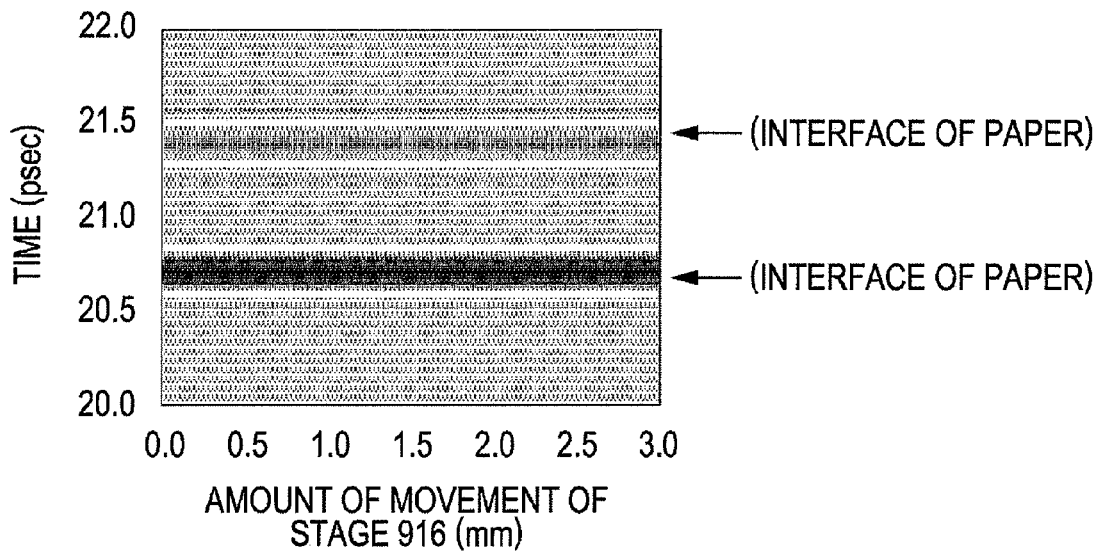
FIG. 12 is a diagram showing an image formation result of an output portion according to Example 4.

The series of these operations are conducted over a region in which an image is formed. When all inspection is completed, the output portion 107 produces an image on the basis of the inspection result and provides it to the user (S1007). FIG. 12 shows an example of production of the image provided by the output portion 107 to the user. FIG. 12 is a tomographic image in a paper thickness direction, and paper interfaces can be recognized. Furthermore, it is recognized that the thickness resolution exceeds about 30 µm by converting the pulse width shown in FIG. 11C to a distance.

According to the present example, in the inspection of the object to be measured 111, the imaging inspection can be conducted while an influence of steam in the air is suppressed. Therefore, a unit which has been previously necessary for adjusting the environment becomes unnecessary, and the inspection can be conducted in a free space. Since the unit for adjusting the environment is unnecessary, miniaturization and price reduction of the apparatus become easy. Furthermore, since the inspection can be conducted in a free space, the versatility of the apparatus of the present example can be improved. Moreover, as shown in FIG. 11C, the time resolution of the terahertz wave can be improved as compared with the state shown in FIG. 11A by using a perfect reflection waveform of the terahertz wave as the second answer signal.

Example 5

The present example relates to a terahertz wave inspection apparatus which suppresses a secular change in the measurement environment, shown in the fourth embodiment. In particular, the present example relates to an imaging inspection apparatus. For more detail, Example 4 is an example in which paper is measured as the object to be measured 111, whereas an example in which a Teflon sheet is measured is shown here. Therefore, explanations of the same parts as those in Example 4 will not be provided.

The object to be measured 111 is a Teflon sheet having a thickness of 25 µm. The measurement condition acquisition portion 108 monitors a temperature and a humidity during inspection. The answer signal storage portion 109 stores answer signals from a mirror perfectly reflecting the terahertz wave under predetermined environments (temperature and humidity). The steps after the measurement is started until the measurement result is provided to the user are the same as those in Example 4 and, therefore, explanations thereof will not be provided.

Figure 16:
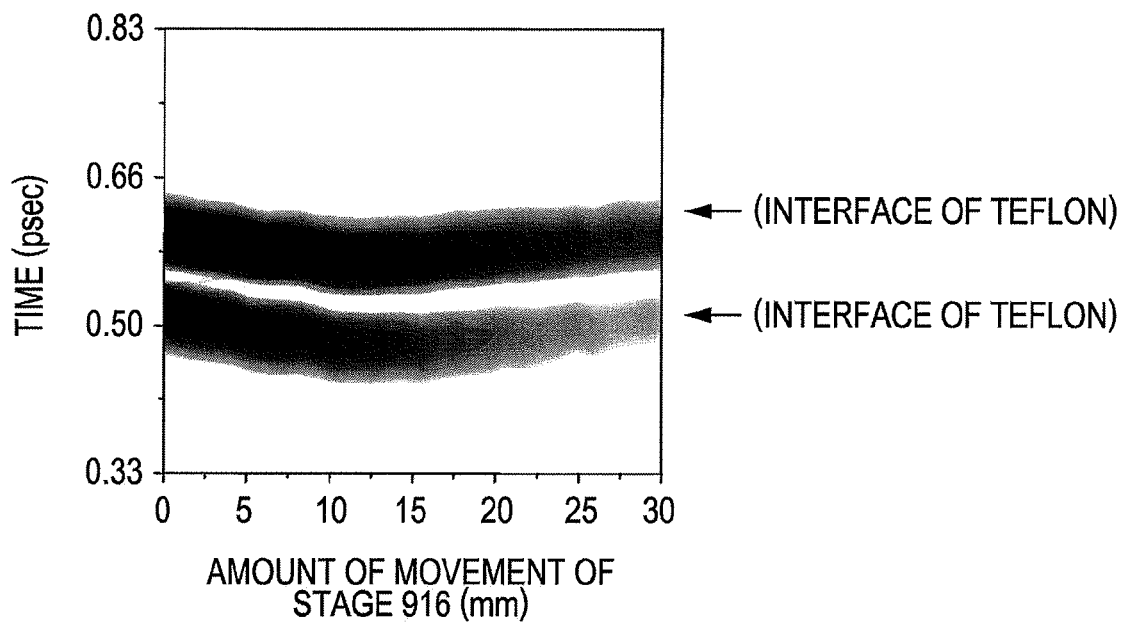
FIG. 16 is a diagram showing an image formation result of an output portion according to an Example 5.
Figure 17:
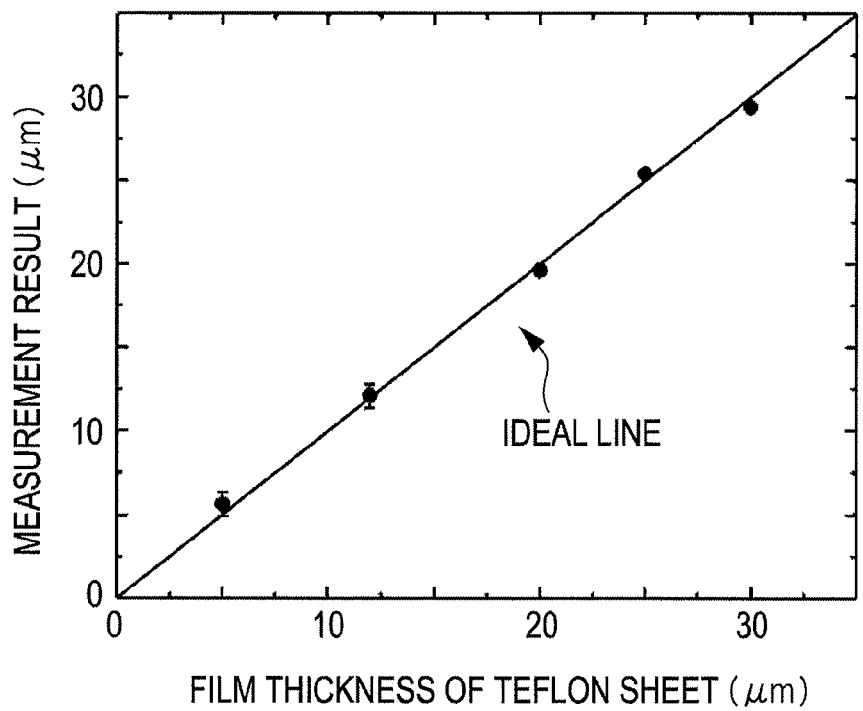
FIG. 17 is a diagram for explaining thickness resolution of an inspection apparatus according to Example 5.

FIG. 16 is a tomographic image in a Teflon sheet thickness direction, and Teflon interfaces can be recognized. When the time information shown in FIG. 16 is converted to a distance in consideration of the refractive index of Teflon, the distance between the interfaces is about 25 µm. In FIG. 17, the distances between the interfaces based on the measurement result are plotted regarding the Teflon sheets having different thicknesses. In FIG. 17, the horizontal axis indicates actually measured film thickness of the Teflon sheet, and the vertical axis indicates the film thickness acquired from the above-described measurement. The straight line described in FIG. 17 is an ideal line. For example, in the case where the actually measured film thickness and the film thickness determined from the above-described measurement are equal, the measurement result is plotted on this ideal line. According to FIG. 17, in the case where the Teflon sheets having thickness of 5 µm to 30 µm are measured, the measurement results are plotted substantially on the ideal line and, therefore, it is recognized that the film thickness is accurately measured. Consequently, it is recognized that the inspection apparatus according to the present invention has the thickness resolution of up to at least about 5 µm.

According to the present example, in the inspection of the object to be measured 111, the imaging inspection can be conducted while an influence of steam in the air is suppressed. Therefore, a unit which has been previously necessary for adjusting the environment becomes unnecessary, and the inspection can be conducted in a free space. Since the unit for adjusting the environment is unnecessary, miniaturization and price reduction of the apparatus become easy. Furthermore, since the inspection can be conducted in a free space, the versatility of the apparatus of the present example can be improved.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions.

This application claims the benefit of Japanese Application No. 2008-017844 filed Jan. 29, 2008, which is hereby incorporated by reference herein in its entirety.

What is claimed is:

1. An inspection apparatus for conducting inspection of an object to be measured by using a terahertz wave, the inspection apparatus comprising:
    a terahertz wave generation portion;
    a terahertz wave detection portion configured to detect a terahertz wave applied from the terahertz wave generation portion to the object to be measured, the terahertz wave being detected through the object to be measured;
    a waveform shaping portion configured to shape a first answer signal with respect to the terahertz wave by using a signal acquired in the terahertz wave detection portion;
    a measurement condition acquisition portion configured to acquire a first measurement condition;
    an answer signal storage portion configured to store second answer signals associated with measurement conditions;
    a selection portion configured to select the second answer signal from the answer signal storage portion by using the first measurement condition; and
    a signal processing portion configured to conduct deconvolution with respect to the first answer signal on the basis of the second answer signal.

2. The inspection apparatus according to claim 1, wherein the selection portion is configured to select the second answer signal by selecting an answer signal corresponding to a second measurement condition closest to the first measurement condition.

3. The inspection apparatus according to claim 1, further comprising:
    a correlation information storage portion configured to store correlation information of the second answer signal selected by the selection portion; and
    an answer signal adjustment portion configured to adjusting the second answer signal to meet the first measurement condition on the basis of the correlation information.

4. The inspection apparatus according to claim 1, further comprising a comparison information storage portion,
    wherein information acquired from a computation result of the signal processing portion and information in the comparison information storage portion are compared in a comparison portion.

5. The inspection apparatus according to claim 1, further comprising a stage configured to move a position of application of the terahertz wave relative to the object to be measured.

6. An inspection method by using a terahertz wave, the method comprising the steps of:
    shaping a waveform serving as a first answer signal by detecting the terahertz wave applied to an object to be measured, the terahertz wave being detected through the object to be measured; and
    acquiring a measurement condition,
    wherein deconvolution with respect to the first answer signal is conducted by using a second answer signal corresponding to the acquired measurement condition.

7. The inspection method according to claim 6, wherein the deconvolution is conducted after the second answer signal is adjusted on the basis of the measurement condition.

* * * * *